United States Patent
Rampoldi et al.

(10) Patent No.: US 8,927,017 B2
(45) Date of Patent: Jan. 6, 2015

(54) PHARMACEUTICAL PREPARATION CONTAINING GABAPENTIN

(75) Inventors: Luca Rampoldi, Lainate (IT); Alessandro Grassano, Monza (IT)

(73) Assignee: ZAMBON S.p.A., Bresso (IT)

(*) Notice: Subject to any disclaimer, the term of this patent is extended or adjusted under 35 U.S.C. 154(b) by 496 days.

(21) Appl. No.: 13/081,036

(22) Filed: Apr. 6, 2011

(65) Prior Publication Data

US 2011/0189272 A1 Aug. 4, 2011

Related U.S. Application Data

(62) Division of application No. 10/581,367, filed as application No. PCT/EP2004/053233 on Dec. 2, 2004, now abandoned.

(30) Foreign Application Priority Data

Dec. 9, 2003 (IT) .............................. MI2003A2399

(51) Int. Cl.
*A61K 9/26* (2006.01)
*A61K 9/16* (2006.01)
*A61K 9/20* (2006.01)
*A61K 31/195* (2006.01)

(52) U.S. Cl.
CPC ............. *A61K 9/1641* (2013.01); *A61K 9/2077* (2013.01); *A61K 31/195* (2013.01)
USPC ............................ 424/470; 424/464; 424/494

(58) Field of Classification Search
CPC ...................................... A61K 9/16
USPC .......................................... 424/470, 464, 494
See application file for complete search history.

(56) References Cited

U.S. PATENT DOCUMENTS

| | | | |
|---|---|---|---|
| 3,147,187 A | 9/1964 | Playfair et al. | |
| 3,263,006 A | 7/1966 | Gutweiler et al. | |
| 4,443,428 A | 4/1984 | Oshlack et al. | |
| 5,169,645 A | 12/1992 | Shukla et al. | |
| 5,232,704 A | 8/1993 | Franz et al. | |
| 5,429,825 A | 7/1995 | Reo et al. | |
| 5,807,574 A | 9/1998 | Cheskin et al. | |
| 6,488,964 B2 | 12/2002 | Bruna et al. | |
| 6,692,767 B2 * | 2/2004 | Burnside et al. | 424/489 |
| 7,056,951 B2 | 6/2006 | Spireas | |
| 7,192,608 B2 | 3/2007 | Ochiai et al. | |
| 2002/0015730 A1 | 2/2002 | Hoffmann et al. | |
| 2002/0091159 A1 | 7/2002 | Spireas | |
| 2003/0064097 A1 | 4/2003 | Patel et al. | |
| 2006/0039968 A1 | 2/2006 | Manikandan et al. | |

FOREIGN PATENT DOCUMENTS

| | | |
|---|---|---|
| WO | WO 99/59572 | 11/1999 |
| WO | WO 00/01416 | 1/2000 |
| WO | WO 03/002151 A1 | 1/2003 |
| WO | 03/035040 | 5/2003 |
| WO | WO 03/068186 A1 | 8/2003 |
| WO | WO 03/082804 A1 | 10/2003 |

OTHER PUBLICATIONS

Kidokoro et al. (Application of Fluidized Hot-Melt Granulation for the preparation of Granules for Tableting; Properties of Granules and Tablets Prepared by FHMG, Drug Development and Industrial Pharmacy, 28(1), pp. 67-76, 2002).*
I. Joseph, et al., "Indomethacin sustained release from alginate-gelatin or pectin-gelatin coacervates", International Journal of Pharmaceutics, vol. 126, No. 1-2, 1995, pp. 161-168 (English Abstract only), http://cat.inist.fr/?aModele=afficheN&cpsidt=2950933.
Y. Miyagawa, et al., "Controlled-release of diclofenac sodium from wax matrix granule", International Journal of Pharmaceutics, vol. 138, No. 2, 1996, pp. 215-224 (English Abstact only), http://cat.inist.fr/?aModele=afficheN&cpsidt=3181045.
"Polyox (TM) WSR Coagulant", The Dow Chemical Company Material Safety Data Sheet, Feb. 26, 2004, pp. 1-15.
R. D. Young, et al., "Advantages in Energy, Fuel and Investment Savings by Melt-Type Granulation Processes", FAI-ISMA Seminar on Technology of Compound Fertilisers Based on Urea, and Use and Benefication of Low Grade Phosphate Rock 1975, The Fertiliser Association of India, Jan. 10, 1975.
Alan Royce, et al., "Alternative Granulation Technique: Melt Granulation", Drug Development and Industrial Pharmacy, vol. 22, Issue 9 & 10, 1996, pp. 917-924.
T. Schaefer, et al., "Melt Granulation in a Laboratory Scale High Shear Mixer", Drug Development and Industrial Pharmacy, vol. 16, Issue 8, 1990, pp. 1249-1277.
Nadia Passerini, et al., "Preparation and characterisation of ibupofen-poloxamer 188 granules obtained by melt granulation", European Journal of Pharmaceutical Sciences, vol. 15, Feb. 2002, pp. 71-78.
P. Flanders, et al., "The Control of Drug Release From Conventional Melt Granulation Matrices", Drug Development and Industrial Pharmacy, vol. 13, Issue 6, May 1987, pp. 1001-1022.
Motonori Kidokoro, et al., "Effect of Crystallization Behavior of Polyethylene Glycol 6000 on the Properties of Granules Prepared by Fluidized Hot-Melt Granulation (FHMG)", Chemical Pharmacy Bulletin, vol. 51, No. 5, May 2003, pp. 487-493.

* cited by examiner

*Primary Examiner* — Johann R Richter
*Assistant Examiner* — Danielle Sullivan
(74) *Attorney, Agent, or Firm* — Oblon, Spivak, McClelland, Maier & Neustadt, L.L.P.

(57) ABSTRACT

A method for preparing a gabapentin granulate comprising melt granulating gabapentin with polyethylene glycol having a melting point comprised between 50 and 80° C.

14 Claims, No Drawings

PHARMACEUTICAL PREPARATION CONTAINING GABAPENTIN

CROSS-REFERENCE TO RELATED APPLICATIONS

The present application is a continuation of U.S. Ser. No. 10/581,367, filed on Jun. 2, 2006, is a National Stage (371) of PCT/EP04/53233, filed on Dec. 2, 2004, which claims priority to MI2003A002399, filed on Dec. 9, 2003.

The present invention relates to a pharmaceutical composition containing gabapentin. Gabapentin is the common name of the 1-aminomethyl-cyclohexane-acetic acid, a known drug with anti-epileptic activity.

The drug is not protected by patent, nevertheless in the U.S. Pat. No. 6,054,482 in the name of Gödecke AG stable pharmaceutical compositions of gabapentin are claimed which maintain, for one year at 25° C. and 60% r.h., the content of the corresponding lactam (a known toxic product which can be generated by gabapentin by dehydration) lower than 0.5% by weight and which have a content of anions of mineral acids lower than 20 ppm.

In the same patent a series of additives, which have to be avoided in the composition because they favour the formation of lactam, is listed as well. They are: modified cornstarch, croscarmellose sodium, glyceric esters of behenic acid, copolymers of metacrylic acid (type A and C), anion-exchange resins, titanium dioxide, silica gel and PEG with low molecular weight.

On the contrary, in the U.S. Pat. No. 6,531,509 in the name of Teva Pharmaceuticals Industries Ltd. it is reported that the invention described in the Gödecke AG patent mentioned above is wrong and that stable compositions of gabapentin can be obtained even when the content of anions of mineral acids in the latter is greater than 20 ppm.

However, no data are provided in this regard, nor the criteria for choosing suitable additives are shown.

In the patent application n. WO 02/26263 in the name of Sigmapharm stable compositions of gabapentin are described containing a stabilizer comprising a compound able to reduce the ionic strength, and at least 20 ppm of one anion of mineral acid.

The stabilizers belong to the following classes: volatile alcohols, non-volatile alcohols, non-volatile liquids, water miscible solids or liquids, immiscible solids or liquids, liquid or solid surface active agents, antioxidants, ketones or aldehydes.

Currently, gabapentin is proposed with different dosages and in two pharmaceutical forms for oral use: capsules and tablets.

Nevertheless, the industrial production of gabapentin tablets has several drawbacks due to the difficulty of compressing the raw material.

Therefore, it is necessary to use the new granulation.

However, this procedure too is not deprived of practical problems since by granulating with water, under different experimental conditions and with different procedures, the formation of a hydrate is always obtained, with consequent loss in the original crystalline structure. An industrial granulation with organic solvents puts some limitations by obliging to use particular plants to protect operators and environment.

Now we have found that the problems mentioned above are overcome by granulating gabapentin with PEG (polyethylene glycol) with a melting point comprised between 50 and 80° C.

Therefore, it is an object of the present invention a gabapentin granulate obtained by granulating gabapentin with PEG having a melting point comprised between 50 and 80° C. The so-obtained granulate can be used as such for preparing tablets or it can be supplemented with other additives and then compressed.

If desired, it is also possible to add to gabapentin and to PEG, before the granulation, additives useful for the subsequent compression or for the disgregation of the tablet such as glydants or disgregants, specific examples being the silica gel, the pregelatinized starch and the croscarmellose sodium.

It is important noting that in the U.S. Pat. No. 6,054,482 mentioned above said substances are included in the ones designated as destabilizing substances of the active principle. On the contrary, we have not noticed any significant degradation of gabapentin (calculated through the quantity of the lactam which has formed) when formulated starting from a granulate according to the present invention and when it contained less or more 20 ppm of an anion of a mineral acid.

Therefore, it is a second object of the present invention a gabapentin granulate obtained by granulating the gabapentin with PEG having the melting point comprised between 50 and 80° C. and additives chosen among glydants, disintegrants and diluents.

Preferably, and this constitutes an additional object of the invention, the granulate will contain a high quantity of gabapentin, for example higher than 80% by weight or even higher than 90% by weight and it can reach even 98% by weight, the remaining 2% being the PEG. The usable PEG is the one commonly used in the pharmaceutical field and it is not necessary using particular pure PEGs. If desired, PEG mixtures with different average molecular weight can be used so that the melting point of the mixture is comprised between 50 and 80° C. Hereinafter under the PEG term, a single PEG or a PEG mixture having the melting point comprised between 50 and 80° C. will be designated indifferently.

The granulate can be prepared by using rotogranulators available on the market, such as, for example, the fast rotogranulators (high shear mixer) produced by the Zanchetta firm, Rotojunion 10 model, or similar devices such as Glatt, Collette, Diosna.

The pharmaceutical compositions in tablets can be prepared by direct compression of the granulate or by adding to the granulate, before the compression, additives of typical pharmaceutical use which give to the tablet properties useful both in the industrial preparation and in the regular therapeutic effect of the drug administered therewith.

Examples of such additives are disintegrants, lubricants and glydants.

Usually, when one wishes to add other additives to the granulate, the composition of the tablet resulting from the mixture compression will be comprised within the following values:

| | |
|---|---|
| granulate | 70-100% by weight, preferably 80-100% |
| additives | 0-30% by weight, preferably 0-20% |

Therefore, it is an object of the present invention gabapentin tablets containing between 70 and 100% by weight of a granulate as described above and between 0 and 30% by weight, preferably between 0 and 20% of additives for pharmaceutical use.

Since the granulate of the invention does not cause the degradation of the active principle and since one of the gabapentin pharmaceutical forms for oral use is constituted by capsules containing it, the granulate itself can be used successfully for the preparation of capsules. Therefore, it is a further object of the present invention the use of the granulate as described above for the preparation of gabapentin capsules and the capsules containing it.

In order to better illustrate the present invention, the following examples are now provided.

EXAMPLE 1

General Procedure for the Granulate Preparation

A mixture of powders constituted by gabapentin, PEG and, in case, other additives is charged in a Zanchetta rotogranulator, Rotojunior 10 model.

The total amount of powders which can be charged in the apparatus mentioned above is comprised between 0.8 and 3 kg and 1-2 kg are preferably charged.

The powders are mixed in the rotogranulator for 5 minutes at 25° C., the blade speed being 100 rpm.

Then, the mixture under stirring is heated until the PEG melting point (between 50 and 80° C.) with the blade speed comprised between 150 and 400 rpm, preferably 300 rpm, and the crusher speed comprised between 600 and 1200 rpm, preferably, 1000 rpm. It is left for a time comprised between 30 and 60 minutes, preferably 45 minutes.

The mixture is then cooled at 25° C. by keeping it under stirring with the blade speed of 100 rpm and the crusher speed of 1000 rpm.

The so-obtained granulated is discharged which, independently from the quantity of the introduced materials, can have a composition comprised within the following values:

| Gabapentin | 70-98% by weight |
| PEG | 2-25% by weight |
| Additives | 0-20% by weight |
| the total being 100%. | |

EXAMPLE 2

With the procedure described in the example 1 the granulates having the following composition have been prepare:

Gr 1

| Gabapentin | 90% |
| PEG 6000 | 6% |
| Modified cornstarch | 4% |

Gr 2

| Gabapentin | 88% |
| PEG 4000 | 2% |
| Modified cornstarch | 10% |

Gr 3

| Gabapentin | 90% |
| PEG 1500 | 1% |
| PEG 4000 | 4% |
| Croscarmellose sodium | 5% |

The so-produced granulates have optimum sliding and compressibility properties (rest angle 30-35% and Carr index 10-18%); the appearance of gabapentin degradation products is not found and, from the FT-Raman analysis, the gabapentin keeps its original crystalline form.

EXAMPLE 3

The granulates according to the invention can be used for obtaining pharmaceutical tablets by using usual compressors.

The mixtures suitable for obtaining tables are comprised in the following values:

| granulate | 70-100% by weight |
| additives | 0-30% by weight |

Co 1

| Gr 1 granulate (see example 2) | 85% |
| pregelatinized starch | 13.5% |
| colloidal silica | 0.5% |
| stearate magnesium | 0.5% |
| titanium dioxide | 0.5% |

Co 2

| Gr 3 granulate | 87% |
| croscarmellose sodium | 11.5% |
| colloidal silica | 0.5% |
| stearate magnesium | 0.5% |
| titanium dioxide | 0.5% |

Co 2

| Gr 2 granulate | 85% |
| copolymer of the metacrylic acid (type C) | 10% |
| stearate magnesium | 0.5% |
| titanium dioxide | 0.5% |
| glyceric esters of the behenic acid | 4% |

Co 4

The Gr 1 granulate described in the example 2 is compressed without adding additional additives to obtain tablets.

Co 5

| Gr 1 granulate | 99% |
| colloidal silica | 0.5% |
| stearate magnesium | 0.5% |

Co 6

| Gr 3 granulate | 85% |
| PEG 4000 | 5% |
| copolymer of the metacrylic acid (type A) | 10% |

The so-obtained tablets show technological properties suitable for a pharmaceutical use (hardness 10-12 Kn, friability <0.1%, disgregation time comprised between 10 and 25', usually <15') and do not show degradation of the active principle or variations of the crystalline form. They are also suitable for a subsequent possible coating.

EXAMPLE 4

The granulates identified as Gr 1 and Gr 2 in the example 2 have been used separately to fill-in gelatine capsulae by obtaining gabapentin pharmaceutical forms in capsules (Cap 1 and Cap 2) Similarly, capsules containing the following compositions have been prepared:

Cap 3

| | | |
|---|---|---|
| Gr 1 granulate | 95% | |
| cornstarch | 4.5% | |
| colloidal silica | 0.5% | |

Cap 4

| | | |
|---|---|---|
| Gr 3 granulate | 98.5% | |
| glyceril behenate | 0.5% | |
| colloidal silica | 1% | |

Cap 5

| | | |
|---|---|---|
| Gr 1 granulate | 86% | |
| croscarmellose sodium | 10% | |
| titanium dioxide | 1% | |
| cornstarch | 4.5% | |

What we claim is:

1. A method for preparing a gabapentin granulate comprising melt granulating gabapentin with polyethylene glycol having a melting point comprised between 50 and 80° C.

2. The method according to claim 1, wherein the gabapentin is present in an amount higher than 80% by weight based on the total weight of the granulate.

3. The method according to claim 1, wherein the gabapentin is present in quantities higher than 90% by weight based on the total weight of the granulate.

4. The method according to claim 1, wherein the gabapentin is present in quantities equal to 98% by weight based on the total weight of the granulate, the polyethylene glycol being 2% by weight based on the total weight of the granulate.

5. A method for producing a gabapentin pharmaceutical composition in a tablet form comprising
preparing a gabapentin granulate according to claim 1, and compressing said granulate into a tablet form.

6. A method for producing a gabapentin pharmaceutical composition in a capsule form comprising
preparing a gabapentin granulate according to claim 1, and filling a capsule with said granulate.

7. The method according to claim 5, wherein said compressing further incorporates at least one known additive useful for the preparation of tablets.

8. The method according to claim 7, wherein said additive is selected from the group consisting of a diluent, a lubricant, a disintegrant and a glydant.

9. The method according to claim 7, wherein said additive represents between 0 and 30% by weight of the tablet, the remaining to 100% being said granulate.

10. The method according to claim 6, wherein said filling further incorporates at least one known additive useful for the preparation of a pharmaceutical in a capsule form.

11. The method according to claim 10, wherein said additive represents between 0 and 30% by weight of the capsule content, the remaining to 100% being said granulate.

12. The method according to claim 1, wherein said melt granulating further comprises one or more additives known for the preparation of solid pharmaceutical forms chosen among tablets and capsules in addition to said gabapentin and said polyethylene glycol having a melting point comprised between 50 and 80° C.

13. The method according to claim 12, wherein said additive is selected from the group consisting of a diluent, a lubricant, a disgregant and a glydant.

14. The method according to claim 12, wherein said granulate has the following composition, wherein the % by weight is based on the total weight of the composition:

| | |
|---|---|
| gabapentin | 70-98% by weight |
| polyethylene glycol | 2-25% by weight |
| additives | 0-20% by weight. |

* * * * *